United States Patent
Nativ et al.

(10) Patent No.: US 10,278,703 B2
(45) Date of Patent: May 7, 2019

(54) TEMPORARY FIXATION TOOLS FOR USE WITH CIRCULAR ANASTOMOTIC STAPLERS

(71) Applicant: Ethicon, Inc., Somerville, NJ (US)

(72) Inventors: Nir I. Nativ, West Orange, NJ (US); Yufu Li, Bridgewater, NJ (US); John Matonick, Warren, NJ (US); Glenn Cook, Clinton, NJ (US); Michael Logue, New Hope, PA (US)

(73) Assignee: Ethicon, Inc., Somerville, NJ (US)

( * ) Notice: Subject to any disclaimer, the term of this patent is extended or adjusted under 35 U.S.C. 154(b) by 451 days.

(21) Appl. No.: 15/075,780

(22) Filed: Mar. 21, 2016

(65) Prior Publication Data
US 2017/0265867 A1    Sep. 21, 2017

(51) Int. Cl.
*A61B 17/115* (2006.01)
*A61B 17/072* (2006.01)
*A61B 17/10* (2006.01)

(52) U.S. Cl.
CPC ........ *A61B 17/1155* (2013.01); *A61B 17/072* (2013.01); *A61B 17/07292* (2013.01); *A61B 17/105* (2013.01); *A61B 2017/07257* (2013.01); *A61B 2017/07278* (2013.01); *A61B 2017/1157* (2013.01)

(58) Field of Classification Search
CPC .......... A61B 17/1155; A61B 17/07292; A61B 17/105; A61B 17/072; A61B 2017/1157; A61B 2017/07278; A61B 2017/07257
See application file for complete search history.

(56) References Cited

U.S. PATENT DOCUMENTS

| | | | |
|---|---|---|---|
| 5,271,544 A | 12/1993 | Fox et al. | |
| 5,311,949 A * | 5/1994 | Chapin | H01H 9/063 173/170 |
| 5,752,965 A * | 5/1998 | Francis | A61B 17/07207 227/178.1 |

(Continued)

FOREIGN PATENT DOCUMENTS

| | | |
|---|---|---|
| EP | 1825820 | 8/2007 |
| EP | 2517637 | 10/2012 |

(Continued)

OTHER PUBLICATIONS

US 8,152,042 B2, 04/2012, Bettuchi et al. (withdrawn)

*Primary Examiner* — Alexander M Valvis
*Assistant Examiner* — Mobeen Ahmed
(74) *Attorney, Agent, or Firm* — David R. Crichton; Leo B. Kriksunov

(57) ABSTRACT

The present invention relates to circular anastomosis stapler and kits comprising reinforcing buttress materials and fixation tools that are slidably installed on the anvil shaft of such staplers which provides a temporary mechanical fixation of a reinforcing buttress to the anvil surface of a circular stapler during the insertion of the anvil into the tubular tissue. When the anvil, loaded with the buttress, is in the desired location, the fixation tool is pulled back along the anvil shaft and removed. The shaft is then connected to the stapling head and the stapling is performed. The present invention also relates to methods for using the kits and devices therein.

4 Claims, 12 Drawing Sheets

(56) References Cited

U.S. PATENT DOCUMENTS

| | | | |
|---|---|---|---|
| 6,874,669 B2* | 4/2005 | Adams | A61B 17/072 227/175.1 |
| 6,939,358 B2* | 9/2005 | Palacios | A61B 17/07207 606/151 |
| 7,128,748 B2 | 10/2006 | Mooradian et al. | |
| 7,793,813 B2 | 9/2010 | Bettuchi | |
| 8,967,448 B2 | 3/2015 | Carter et al. | |
| 9,010,612 B2 | 4/2015 | Stevenson et al. | |
| 9,161,757 B2 | 10/2015 | Bettuchi | |
| 9,839,420 B2* | 12/2017 | Shelton, IV | A61B 17/068 |
| 9,895,151 B2* | 2/2018 | Milliman | A61B 17/1155 |
| 2004/0254590 A1* | 12/2004 | Hoffman | A61B 17/1114 606/139 |
| 2005/0070929 A1* | 3/2005 | Dalessandro | A61B 17/07207 606/151 |
| 2005/0228446 A1* | 10/2005 | Mooradian | A61B 17/115 606/215 |
| 2006/0085034 A1* | 4/2006 | Bettuchi | A61B 17/115 606/219 |
| 2006/0135992 A1* | 6/2006 | Bettuchi | A61B 17/072 606/219 |
| 2006/0173470 A1* | 8/2006 | Oray | A61B 17/07207 606/151 |
| 2007/0203509 A1* | 8/2007 | Bettuchi | A61B 17/07292 606/153 |
| 2008/0035700 A1* | 2/2008 | Huang | B25C 1/003 227/120 |
| 2009/0095791 A1* | 4/2009 | Eskaros | A61B 17/072 227/175.1 |
| 2009/0104861 A1* | 4/2009 | Van Der Linde | B25F 5/02 451/344 |
| 2009/0206143 A1* | 8/2009 | Huitema | A61B 17/07207 227/176.1 |
| 2010/0001034 A1* | 1/2010 | Huang | B25C 1/04 227/120 |
| 2010/0252293 A1* | 10/2010 | Lopano | B25F 5/02 173/170 |
| 2012/0241499 A1* | 9/2012 | Baxter, III | A61B 17/07207 227/176.1 |
| 2012/0289979 A1* | 11/2012 | Eskaros | A61B 17/07292 606/151 |
| 2013/0068819 A1 | 3/2013 | Viola | |
| 2013/0146643 A1* | 6/2013 | Schmid | A61B 17/0682 227/180.1 |
| 2013/0153639 A1* | 6/2013 | Hodgkinson | A61B 17/1114 227/180.1 |
| 2014/0097224 A1 | 4/2014 | Prior | |
| 2014/0217147 A1* | 8/2014 | Milliman | A61B 17/07292 227/179.1 |
| 2016/0278774 A1* | 9/2016 | Shelton, IV | A61B 17/068 |
| 2016/0287254 A1* | 10/2016 | Baxter, III | A61B 17/068 |
| 2017/0056017 A1* | 3/2017 | Vendely | A61B 17/07292 |

FOREIGN PATENT DOCUMENTS

| | | |
|---|---|---|
| EP | 2620107 A1 | 7/2013 |
| EP | 2604197 | 9/2015 |

* cited by examiner

TEMPORARY FIXATION TOOLS FOR USE WITH CIRCULAR ANASTOMOTIC STAPLERS

FIELD OF THE INVENTION

The present invention relates to surgical instruments and methods for enhancing properties of tissue repaired or joined by surgical staples and, more particularly to surgical instruments and methods designed to enhance the properties of repaired or adjoined tissue at a target surgical site, especially when sealing an anastomosis between adjacent intestinal sections.

BACKGROUND OF THE INVENTION

Throughout the years the medical field has utilized various techniques to join or bond body tissue together. Historically, suturing was the accepted technique for rejoining severed tissues and closing wounds. Suturing has traditionally been achieved with a surgical needle and a suturing thread, and more recently, with a variety of polymeric or metallic staples. The intended function of sutures is to hold or approximate the edges of a wound or tissue against one another during the healing process so as to reduce discomfort, pain, scarring and the time required for healing. Staples have recently been used to replace suturing when joining or anastomosing various body structures, such as, for example, the bowel. The surgical stapling devices employed to apply these staples are generally designed to simultaneously cut and seal an extended segment of tissue in a patient.

Linear or annular surgical stapling devices are employed by surgeons to sequentially or simultaneously apply one or more rows of surgical fasteners, e.g., staples or two-part fasteners, to body tissue for the purpose of joining segments of body tissue together and/or for the creation of an anastomosis. Linear surgical stapling devices generally include a pair of jaws or finger-like structures between which body tissue to be joined is placed. When the surgical stapling device is actuated and/or "fired," firing bars move longitudinally and contact staple drive members in one of the jaws, and surgical staples are pushed through the body tissue and into and against an anvil in the opposite jaw thereby crimping the staples closed. A knife blade may be provided to cut between the rows/lines of staples.

Annular surgical stapling devices generally include an annular staple cartridge assembly including a plurality of annular rows of staples (typically two or three), an anvil assembly operatively associated with the annular cartridge assembly, and an annular blade disposed internal of the rows of staples. In general, an end-to-end anastomosis stapler typically places an array or group of staples into the approximated sections of a patient's bowels or other tubular organs. The resulting anastomosis contains an inverted section of bowel which contains numerous "B" shaped staples to maintain a secure connection between the approximated sections of bowel.

Anastomotic leaks may result in morbidity and frequently death. In addition to the use of surgical staples, sealants, e.g., synthetic or biological sealants, can be applied to the surgical site to guard against leakage. The biological sealants are typically applied to the outer surface of the anastomosis using a dual lumen syringe or spray nozzle in a separate step. The delivery of the sealant can be compromised by an inability to get at or between individual staple sites, and along staple lines and tissue seams.

U.S. Pat. No. 7,793,813 titled "Hub for positioning annular structure on a surgical device" discloses an assembly for disposing an annular structure between adjacent intestinal sections, the assembly comprising: a) an annular surgical stapling device having an anvil assembly and a tubular body portion, the anvil assembly having an anvil member and an anvil shaft, the tubular body portion carrying a plurality of surgical staples in an annular configuration, the tubular body portion having a connection member disposed radially inward of the surgical staples, the anvil shaft of the anvil member including a flange and being attachable to the connection member of the tubular body portion; and b) a hub adapted for support on the anvil shaft to engage the flange of the anvil shaft, the hub including a central sleeve defining a lumen therethrough for selectively receiving the anvil shaft therein, and an annular structure radially extending from the central sleeve, the annular structure including an outer annular disc defining a central opening having a dimension larger than an outer diameter of the central sleeve and a web interconnecting the disc to the central sleeve, wherein the central sleeve comprises at least one resilient finger extending substantially in a longitudinal direction, and wherein, when the hub is supported on the anvil shaft, the at least one resilient finger engages the flange of the anvil shaft to position the annular structure at a location spaced a distance from a tissue contacting surface of each of the anvil assembly and the tubular body portion.

U.S. Pat. No. 9,161,757 titled "Hub for positioning annular structure on a surgical device" discloses a method of disposing an annular structure between adjacent tissue sections, the method comprising the steps of: a) providing a surgical stapling device including an anvil assembly and a body portion, the anvil assembly including an anvil member supported on an anvil shaft and the body portion carrying a plurality of surgical staples and a knife; b) providing a hub for locating an annular structure between the adjacent tissue sections, the hub including a central sleeve having a first end and a second end defining a lumen therebetween, the central sleeve configured to selectively receive and engage the anvil shaft of the anvil assembly, and an annular structure extending from the first end of the central sleeve and extending radially outwardly therefrom; c) inserting the anvil assembly into a first tissue section such that the anvil member is positioned adjacent to a first side of the first tissue section; d) after the anvil assembly is inserted into the first tissue section, positioning the hub onto the anvil shaft by inserting the anvil shaft through the first end of the hub and towards the second end of the hub such that the annular structure is concentrically located with respect to a longitudinal axis of the anvil shaft and such that the annular structure is positioned immediately adjacent to a second side of the first tissue section that is opposed to the first side of the first tissue section; e) inserting the body portion into a second tissue section; f) approximating the anvil assembly, hub and body portion with one another so that an end portion of the first tissue section, an end portion of the second tissue section and the annular structure are disposed between the anvil member and the body portion; and g) connecting the anvil assembly to the surgical stapling device so that a proximal end of the anvil shaft is connected to a connection member mounted within the body portion of the surgical stapling device, wherein the annular structure is disposed between the first tissue section and the second tissue section.

U.S. Pat. No. 7,128,748 titled "Circular stapler buttress combination" discloses a combination medical device comprising: a) a circular stapler instrument, comprising a staple cartridge component having a central recessed aperture and corresponding anvil component having a central recessed aperture, and b) one or more portions of buttress material adapted to be a) stably positioned upon the staple cartridge and/or anvil components of the stapler instrument prior to, or at the time of, use, b) while in position upon the stapler instrument component(s), to then be delivered to a tissue site in combination with the stapler instrument components, c) upon delivery of the components and positioned material portion(s) to the tissue site, to provide a first region of buttress material as a staple line buttress seal between joined tissue sections upon activation of the stapler instrument, and optionally, d) to permit the removal of one or more portions of a second region of the buttress material upon activation of a stapler instrument knife provided by the stapler instrument, wherein the buttress material portion adapted to fit the cartridge component comprises a circumferential disc having an integral raised center portion adapted to fit the central recessed aperture of the cartridge, and the buttress material portion adapted to fit the anvil component comprises a circumferential disc having an integral raised center portion adapted to fit the central recessed aperture of the anvil.

U. S. Patent Application publication No. 2014/0097224 titled "Buttress Fixation for a Circular Stapler" discloses a circular stapling apparatus, comprising: an anvil assembly with an anvil member and a shaft; a tubular body portion having a staple cartridge, the shaft of the anvil assembly being connectable to the tubular body portion so that the anvil assembly is movable toward and away from the tubular body portion, the staple cartridge including a plurality of staple and a pusher having a fingers for driving the staples, at least one of the fingers including a protrusion; a buttress material removably attached to the anvil assembly, staple cartridge, or both, by at least one anchor; and at least one of the anvil assembly and staple cartridge having a notch shaped for retaining the anchor, the pusher being movable to move the protrusion into engagement with the anchor in the notch.

U. S. Patent Application publication No. 2014/0197224 titled "Buttress retainer for EEA anvil" discloses an apparatus for joining two hollow organ sections with an annular array of surgical staples, the apparatus comprising: a staple cartridge assembly including a plurality of surgical staples in an annular array; an anvil assembly including an anvil member and a shaft extending therefrom, the anvil member including a proximal surface defining a plurality of staple pockets for deforming the surgical staples, the anvil assembly movable relative to the staple cartridge assembly between spaced apart and approximated positions to adjustably clamp tissue between the staple cartridge and anvil assemblies; and a buttress assembly including: a ring member configured to engage a knife member, the ring member secured with the anvil member; a buttress member disposed in a superposed relation with the plurality of staple pockets defined in the anvil member; and a retaining member having an attaching member configured to be secured with the ring member to secure the buttress member between the cut ring and the retaining member, and to position the buttress member relative to the anvil assembly.

U.S. Pat. No. 9,010,612 titled "Buttress support design for EEA anvil" discloses an apparatus for joining two hollow organ sections with an annular array of surgical staples, the apparatus comprising: a staple cartridge component including a plurality of surgical staples in the annular array; an anvil component including an anvil member and a shaft extending therefrom, the anvil member defining a plurality of staple pockets for deforming the plurality of surgical staples, the anvil component movable relative to the staple cartridge component between spaced apart and approximated positions to adjustably clamp tissue between the staple cartridge and anvil components; a buttress member concentrically aligned with the plurality of staple pockets defined in the anvil member; and a buttress mount detachably secured with the shaft of the anvil component, the buttress mount including an annular ring member and at least one support member radially extending outward from the annular ring member to secure the buttress member to the anvil member, the at least one support member at least partially underlying the buttress member to provide support thereto, wherein the buttress mount is separate from the buttress member, and the annular ring member of the buttress mount is secured to the shaft of the anvil component.

U. S. Patent Application publication No. 2014/0217147 titled "Circular Stapling Device Including Buttress Material" discloses a circular stapling device, comprising: a handle assembly; an elongate body that extends from the handle assembly; an end effector mounted on a distal end of the elongate body and including a cartridge assembly and an anvil assembly, the anvil assembly including: a circular anvil head that supports a crush ring; an anvil cap that connects to the anvil head, the anvil cap being movable relative to the anvil head between an approximated position and an unapproximated position, the crush ring being spaced from the anvil cap when the anvil cap is disposed in the approximated position and movable into engagement with the anvil cap to move the anvil cap to the unapproximated position, the anvil cap supporting an O-ring; and a circular anvil buttress member including a body portion and an extension portion that extends from the body portion, the body portion supported on a tissue engaging surface of the anvil head, the extension portion being securable between the O-ring and the anvil head when the anvil cap is disposed in the approximated position, the extension portion being releasable from between the O-ring and the anvil head when the anvil cap is disposed in the unapproximated position so that the body portion separates from the tissue engaging surface of the anvil head.

European Patent Application publication No. 2,620,107A1 titled "Surgical device including buttress material" discloses a surgical stapling device for joining tissue portions, comprising: a handle assembly; a tubular body portion supported on a distal end of the handle assembly, the tubular body portion having a staple cartridge assembly containing a plurality of surgical staples in an annular array; an anvil assembly at a distal end of the stapling device, the anvil assembly having a shaft for removably connecting the anvil assembly to the tubular body portion, the anvil assembly and tubular body portion being juxtaposed with respect to one another along the shaft and arranged so as to be approximated with respect to one another; a support member extending from the tubular body portion towards the anvil assembly; and a buttress material supported by the support member and removably attached thereto, the buttress material being disposed between the anvil assembly and the staple cartridge assembly.

U.S. Pat. No. 8,967,448 titled "Surgical stapling apparatus including buttress attachment via tabs" discloses an apparatus for joining two hollow organ sections with an annular array of surgical staples, the apparatus comprising: a staple cartridge component including a plurality of surgical staples arranged in an annular array, the staple cartridge component including an outer wall defining a circumferential groove therein; an anvil component movable relative to the staple cartridge component between spaced apart and approximated positions to adjustably clamp the organ sections between the staple cartridge and anvil components; a buttress component configured and dimensioned to be positioned on a distal surface of the staple cartridge component, the buttress component including a buttress member and a plurality of circumferentially arranged tabs extending proximally from the buttress member, each tab having a length such that the tab extends across the circumferential groove of the staple cartridge component when the buttress member overlies a tissue facing surface of the staple cartridge component; and a fastening member configured and dimensioned to engage the plurality of circumferentially arranged tabs into the circumferential groove of the staple cartridge component to securely position the buttress component on the staple cartridge component.

U. S. Patent Application publication No. 2013/0068819 entitled "Structure Containing Wound Treatment Material", discloses an anvil assembly for a circular stapling apparatus, where the anvil assembly includes an anvil head configured to support an anvil plate thereon; a shaft extending from the anvil head and configured to selectively engage a connection member of the circular stapling apparatus; an anvil plate operatively connected to the anvil head, the anvil plate defining a plurality of staple forming pockets therein; and a wound treatment material disposed in each staple forming pocket of the anvil plate. The wound treatment material is at least one of an adhesive, a sealant, a hemostat and a medicament.

U.S. Pat. No. 8,152,042 entitled "Annular Adhesive Structure" discloses an apparatus for sealing at the anastomotic site. In some embodiments, a washer or structural body is wrapped completely around an anvil shaft, with staples driven through the structural body to release the sealant.

Post-operative leakage of the anastomotic seals has been shown in some instances to lead to morbidity and mortality. A number of technologies are intended to address leakage by reinforcing the tissue using a buttress or a similar reinforcing structure applied to the tissue being joined. However there is a lack of reliable and rapid technique for installation of the buttress and fixation of the buttress immediately prior to stapling tissues and establishment of the anastomotic joint, due to the difficult access to the site and also due to the need to have the devices and methods applicable to a wide variety of anastomotic staplers available to the surgeon. Alternative methods to fixate the buttress by adhesives or retention rings are complex and may result in unreliable separation of the buttress from the anvil. The insertion of the anvil into the tubular tissue remains challenging since the tissue mucosal walls tend to separate the buttress from the anvil surface during insertion. There is a need for devices enabling properly positioning and retaining a buttress prior to anastomotic stapling.

SUMMARY OF THE INVENTION

The present invention relates to surgical instruments and methods for enhancing properties of tissue repaired or joined by surgical staples and, more particularly to surgical instruments and methods designed to enhance the properties of repaired or adjoined tissue at a target surgical site, especially when sealing an anastomosis between adjacent intestinal sections so as to improve tissue viability and to prevent leakage.

Briefly, according to one embodiment of the present invention, use of a buttress or a reinforcing O-ring shaped washer to strengthen an anastomotic joint requires holding the buttress against the anvil during insertion of the anvil into the intestine prior to stapling. A fixation tool that is slidably installed on the anvil shaft (or pin), provides a temporary mechanical fixation of the buttress to the anvil surface of a circular stapler during the insertion of the anvil into the tubular tissue. When the anvil, loaded with the buttress, is in the desired location, the fixation tool is pulled back along the anvil shaft and removed, and no longer supports the buttress. The shaft is then connected to the stapling head and the stapling is performed.

Briefly, according to another embodiment, the fixation tool slides on the anvil shaft and pushes/presses the buttress into the anvil during insertion into the tubular tissue such as intestinal tissue or colon. Bumps or protrusions at the fixation tool interface with the buttress to prevent the buttress from sticking to the fixation tool and from buttress being pulled back from anvil upon removal of the fixation tool. The fixation tool, which has a conical shape adjacent to the anvil, improves insertion and withdrawal.

The present invention, in another embodiment, relates to a circular stapler comprising: a circular anvil having flat facing surface; a staple head assembly with an opposing flat surface; an anvil shaft that joins the anvil and staple head assembly; buttress material positioned on a facing surface; and a fixation tool having at a proximal end an elongated, cylindrical sleeve with an outer circumference and at a distal end a frustoconically shaped flange, wherein an interior axial opening traverses the entire length of the sleeve and the flange, said flange terminating at the distal end with a flat face portion, said flat face portion having a diameter larger than diameter of the cylindrical sleeve and a plurality of bumps disposed on said flat face portion, said sleeve having at least one slit starting at the proximal end and extending along the sleeve towards the flange.

The present invention, in another embodiment, relates to a method of establishing ananastomotic joint between tubular tissue lumens with an anastomotic stapler comprising the steps of: positioning a buttress and a fixation tool on an anvil shaft for a circular stapler; slidably advancing the fixation tool towards anvil on the anvil shaft; immobilizing the buttress against anvil with the fixation tool; temporarily maintaining the fixation tool in a first position on the anvil shaft; inserting the anvil with the buttress and the fixation tool into a first tubular tissue; removing the fixation tool from the first tubular tissue leaving the anvil with the buttress inside the first tubular tissue; approximating the anvil with the buttress disposed within the first tubular tissue to a stapling head which is disposed within a second tubular tissue; compressing the first and the second tubular tissues between the stapling head and the anvil with the buttress disposed between the stapling head and the anvil but within the first tubular tissue; firing the anastomotic stapler, thus establishing a stapled anastomotic joint between the first and the second tubular tissues reinforced by the buttress.

DETAILED DESCRIPTION OF THE INVENTION

Surgery often involves joining of two or more layers of tissue together with optional simultaneous sectioning of a portion of the tissue along the staple line. For example, colorectal surgery in many cases involves the resection of a segment of the colon and rectum. Following a colorectal resection, the colon and rectum are drawn together with a circular stapler and an end-to-end anastomosis is performed. Post-op leakage of the anastomosis has been shown to lead to morbidity and mortality.

Typical surgical stapling instruments have a staple-containing component and an opposing anvil component, between which at least two tissue layers to be joined are compressed prior to delivery of staples from the staple-containing component, whereby staples are piercing both tissue layers and are bent, deformed, or closed against the opposing anvil component.

Figure 1:
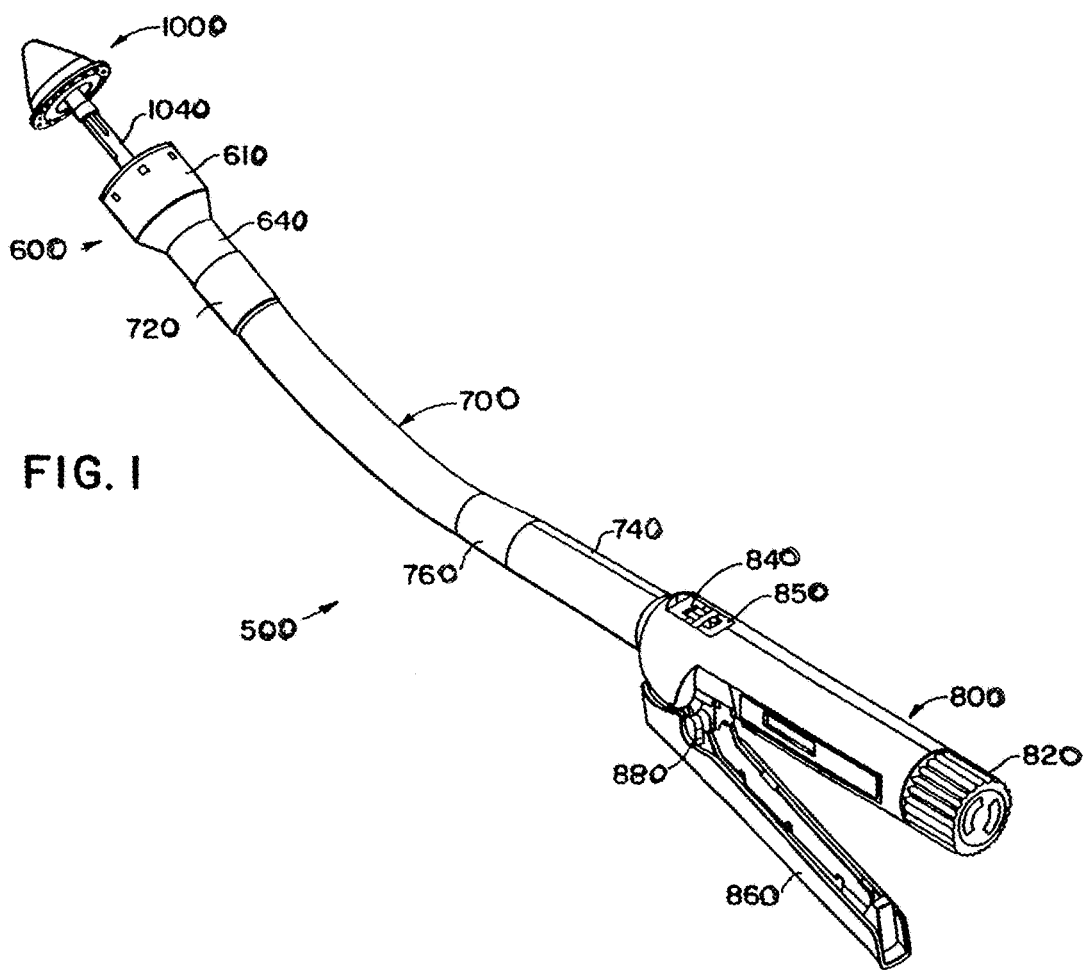
FIG. 1 shows perspective view of a surgical anastomosis stapling instrument or stapling device for performing a circular anastomosis stapling operation.

Referring now to FIG. 1, a generic surgical anastomosis stapling instrument or stapling device for performing a circular anastomosis stapling operation is shown, with the figure taken from the U.S. Pat. No. 5,271,544 "Surgical anastomosis stapling instrument", assigned to Ethicon, Inc., Somerville, N.J., and incorporated herein by reference in its entirety for all purposes. Various modifications and iterations of the shown stapling device are known in the art, having similar features. The circular anastomosis surgical stapling instrument 500 includes a distal stapling head assembly 600 connected by a longitudinally curved support shaft assembly 700 to a proximal actuator handle assembly 800. The stapling instrument includes an anvil assembly or anvil 1000 which is slidable longitudinally relative to the stapling head assembly 600 and mounted on an axially extending moveable shaft 1040. An optional rotatable adjusting knob 820 is provided at the proximal end of the actuator handle assembly 800 for adjusting the spacing between the stapling head assembly 600 and the anvil assembly 1000. An optional movable indicator 840 is visible through an optional window 850 on top of the handle assembly 800 to indicate the staple height selected by rotation of the adjusting knob 820. The indicator 840 is movable indicating that the anvil gap is within a desired operating range of the stapling instrument 500. The position of the indicator 840 also indicates whether the selected staple height is large or small.

A staple actuating lever 860 is pivotally mounted on the actuator handle assembly 800 for driving the surgical staples from the stapling head assembly 600 when the anvil assembly 1000 is closed to provide the desired staple height. A pivotal latching member 880 is mounted on the handle assembly 800 for locking the staple actuating lever 860 against movement to preclude actuation of the stapling head assembly 600 when the anvil gap is outside of a predetermined range. The stapling head assembly 600 includes a tubular casing 610 as well as a hollow tubular connector 640 at the proximal end of the casing 610 which receives the distal end of the support shaft 700. A ferrule or sleeve 720 overlaps the joint between the tubular connector 640 and the distal end of the support shaft 700. The proximal end of the support shaft 700 is received by a tubular extension 740 at the distal end of the actuator handle assembly 800. A ferrule or sleeve 760 overlaps the joint between the proximal end of the support shaft 700 and the distal end of the tubular extension 740. The movable indicator 840 is visible through a window 850 on top of the handle assembly 800 to indicate the staple height selected by rotation of the adjusting knob 820.

Other versions and modifications of the circular surgical stapler are known to a skilled artisan. There are typically at least two and frequently more concentric stapling lines or concentric circular rows of staples-containing slots surrounding shaft 1040, with staples in each row typically staggered or offset relative to the staples in the adjacent row, to improve the sealing and prevent leakage along the stapling line.

The anastomosis can be performed by a variety of techniques known in the art. In one exemplary technique, low anastomosis of colon to rectum using the anastomotic stapler is performed. Briefly, after stapler 500 is inserted through the anus, the descending colon is fixated around anvil 1000, with purse string sutures tied around the shaft and the rectal stump is fixated around stapling head 600 with purse string sutures also tied around the shaft. Anvil 1000 is then pulled towards stapling head 600 and then the staples are deployed to join the tissue of the descending colon and rectal stump at their respective serosal surfaces, with simultaneous action of circular knife or scalpel (not shown) within the stapler 500 cutting away excessive tissue (inverted bowel) closest to shaft 1040, resulting in anastomosis. Stapler 500 is then removed.

Figure 2:
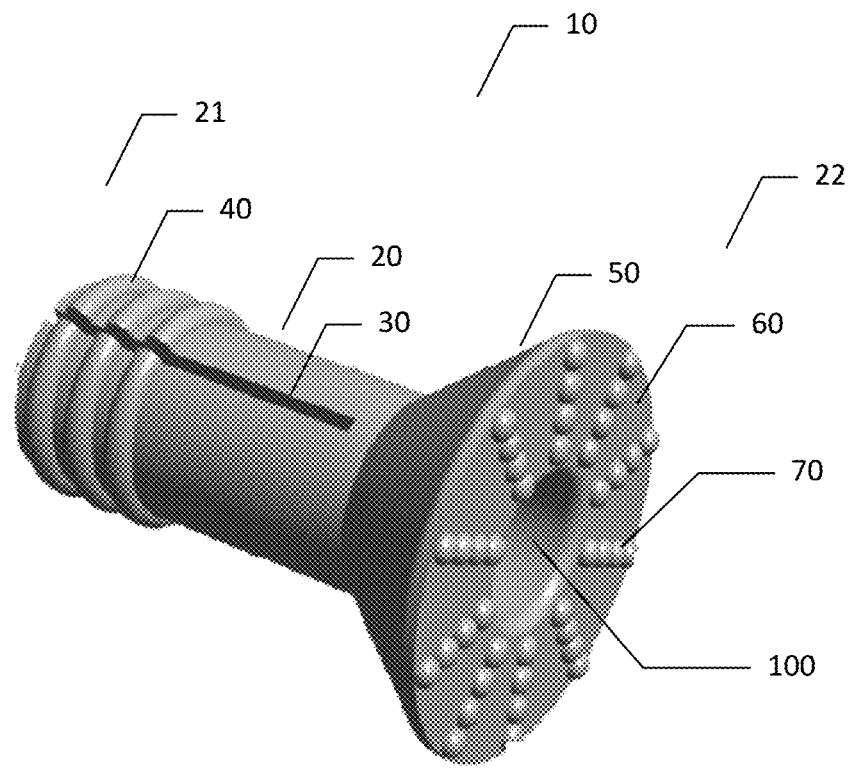
FIG. 2 shows perspective view of temporary fixation tool of the present invention.
Figure 3:
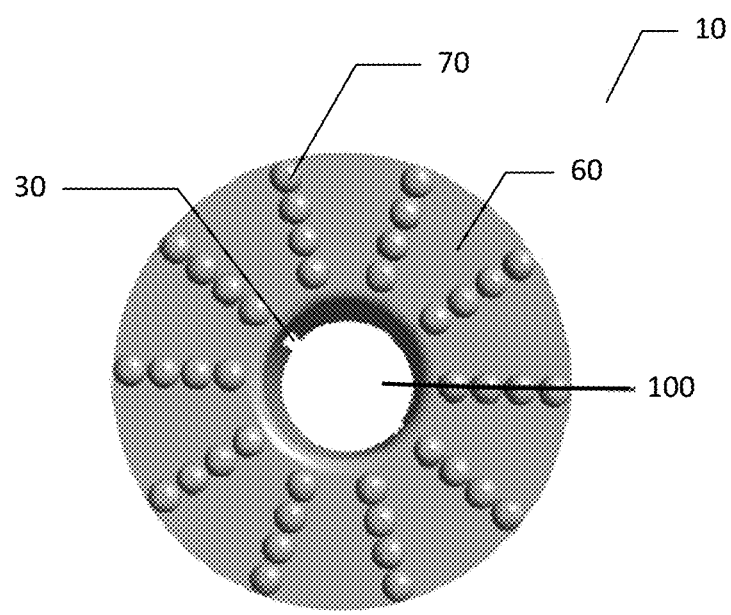
FIG. 3 shows a schematic frontal/perspective view of temporary fixation tool of the present invention.
Figure 4A:
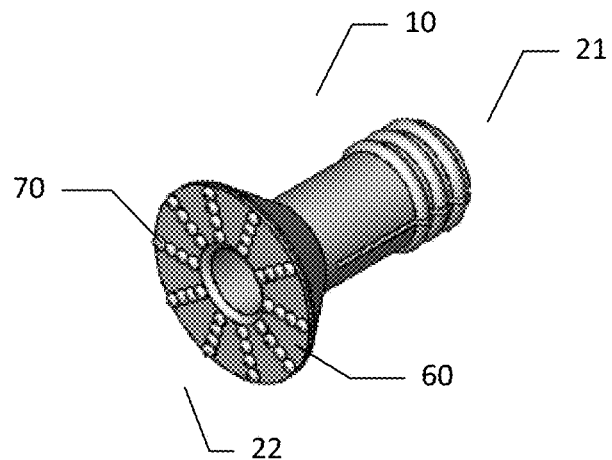
FIG. 4A shows perspective view of temporary fixation tool of the present invention.
Figure 5A:
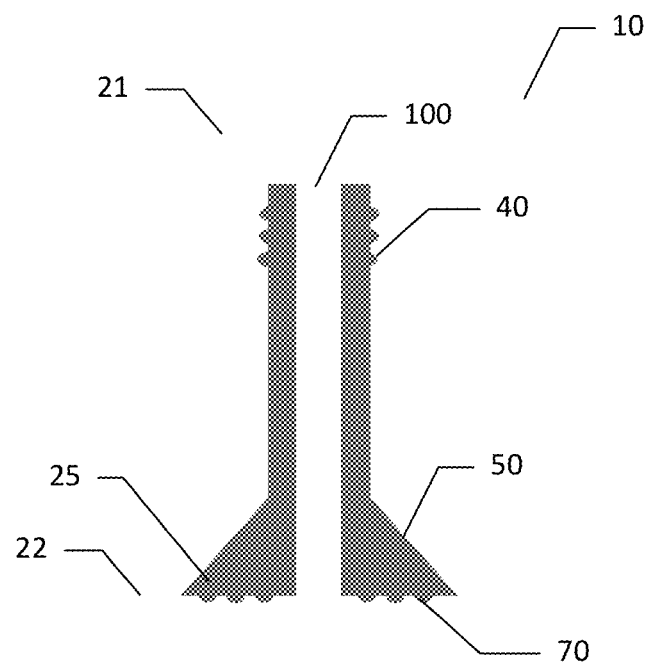
FIG. 5A shows schematic cross-sectional side view of temporary fixation tool of the present invention.

A temporary fixation tool 10 for positioning annular structure such as a buttress for use with circular anastomotic staplers is shown in FIGS. 2 and 4A, in a perspective view, in FIG. 3 in frontal/perspective view, and in FIG. 5A in a schematic side cross-sectional view. Fixation tool 10 comprises an elongated sleeve 20 with a conically shaped flange 50 at a distal end 22. An axial opening 100 traverses sleeve 20 and flange 50 and is sized to slidably fit over the shaft of the circular stapler.

Flange 50 terminates with a flat face portion 60 at distal end 22, with flat face 60 having diameter larger than diameter of sleeve 20 and close to the diameter of stapler anvil 1000 (FIG. 1). Flat face 60 has a plurality of bumps or protrusions 70 with at least 2 bumps more preferably 8 bumps or as many as 200 or up to 1000 bumps 70, such as 20, 30, 40, 60, 80 bumps 70.

Sleeve 20 at a proximal end 21 has optional grips 40, comprising a plurality of raised circumferential ridges 40 or a plurality of circumferential trenches (not shown). In some embodiments, there are 3, 4, or 5 ridges 40. Sleeve 20 has at least one, preferably two or more slits or cuts 30, starting at proximal end 21 and extending through sleeve 20 towards flange 50, but terminating before flange 50. Two slits 30 opposing each other are shown, but 3, 4, 5, 6 or more slits 30 symmetrically disposed on sleeve 20 are contemplated. Slits 30 are sized to enable manual compressing sleeve 20 once fixation tool 10 installed onto anvil shaft 1040 for immobilizing fixation tool 10 on anvil 1000.

Fixation tool 10 is preferably monolithically formed, alternatively it can be assembled by joining flange 50 with sleeve 20. Fixation tool 10 can be made of any suitable inert material, such as polymeric materials, composites, metals, etc., and can be fabricated by injection molding, machining, stamping and the like.

The external diameter of sleeve 20 (not including ridges 40 or trenches) is about 10-100% larger than the diameter of anvil shaft 1040. In some embodiments, the external diameter of sleeve 20 is from about 5 mm to about 10 mm, such as 8 mm.

The length of sleeve 20 is from about 15 mm, to about 60 mm, such as 20 mm, 30 mm, 40 mm.

The diameter of axial opening 100 is sized to slidably fit over the shaft 1040 of the circular stapler, with the diameter of axial opening 100 being from 1% to 10% or 20% larger relative to the diameter of anvil shaft 1040. In some embodiments, the diameter of axial opening 100 is from about 4 mm to about 10 mm, such as 7 mm.

The diameter of flat face 60 is sized to be similar to the largest diameter of anvil 1000, i.e. from about 80% to about 125% of the largest diameter of anvil 1000, such as 90%, 100%, 110% of the largest diameter of anvil 1000. In some embodiments, the diameter of flat face 60 is 20 mm, 22 mm, 25 mm, 30 mm.

Bumps of protrusions 70 are generally spherical or semispherical, or elliptical, with a height from about 0.5 mm to about 4 mm, such as 1 mm, 1.5 mm 2 mm, 3 mm. As shown in the hemispherical embodiment, the height is approximately one half the diameter of the hemisphere.

In some embodiments grips 40 are raised circumferential ridges having semispherical cross-section of 1 to 2 mm diameter, such as 1.6 mm diameter.

Slits 30 are about 0.1 mm to about 1 mm wide, such as 0.5 mm or 0.8 mm wide, and have length from about 50% of the length of sleeve 20 to about 100% of the length of sleeve 20, such as 80% or 90%. In some embodiments, slits 30 are 18 mm, 25 mm or 30 mm long.

Conically shaped flange 50 formed by transition from larger diameter flat face 60 to smaller diameter sleeve 20, with cone angle 25 ranging from about 25 degrees to about 65 degrees, such as 30, 45, 60 degrees cone angle 25. The overall length of fixation tool 10 is about 25-50 mm, such as 30 mm.

Figure 4B:
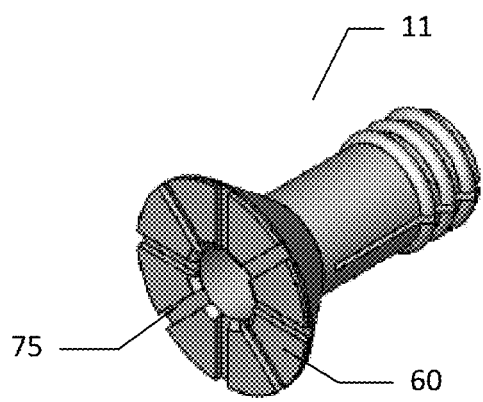
FIGS. 4B and 4C show perspective view of comparative fixation devices.
Figure 4C:
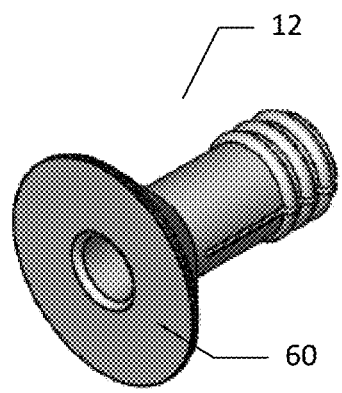

Referring now to FIGS. 4A, 4B, 4C, inventive fixation tool 10 was comparatively tested versus alternative embodiments such as device 11 having trenches 75 in flat face 60 (FIG. 4B), or device 12 having no features in flat face 60 (FIG. 4C). The inventors discovered that the comparative devices failed to secure buttress or separate from the buttress in the animal testing of GI circular anastomosis, while the inventive fixation tool 10 having 10 arrays of 4 semispherical bumps as shown, performed well.

Figure 5B:
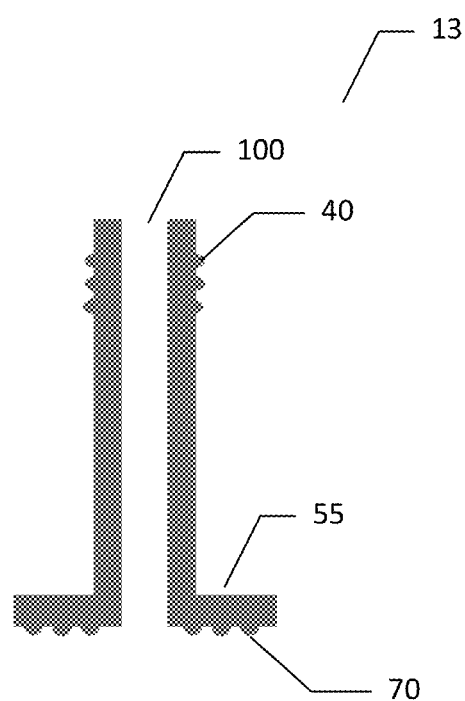
FIG. 5B shows schematic cross-sectional side view of comparative fixation device.

Referring now to FIGS. 5A, 5B, inventive fixation tool 10 was comparatively tested versus alternative embodiments such as device 13 (FIG. 5B), having the overall structure and the same bumps 70 but having flange 55 that is not a conically shaped flange as flange 50 of inventive fixation tool 10. The inventors discovered that comparative device 13 failed to adequately secure buttress or separate from the buttress in the animal testing of GI circular anastomosis, while inventive fixation tool 10 having conically shaped flange 50, performed well.

Figure 6A:
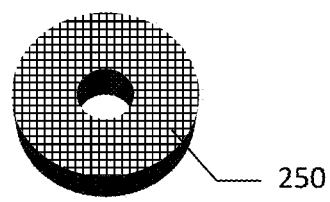
FIG. 6A shows perspective view of a buttress.
Figure 6B:
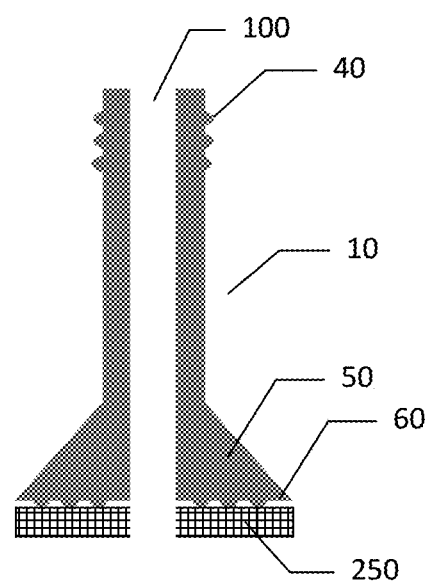
FIGS. 6B, 6C, 6D show schematic cross-sectional side views of temporary fixation tool positioned against buttress.
Figure 6C:
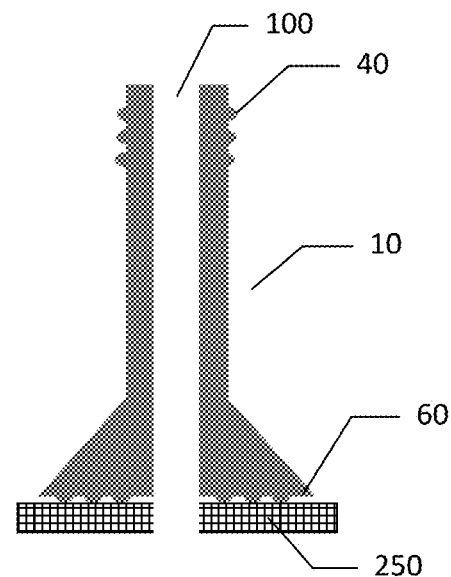
Figure 6D:
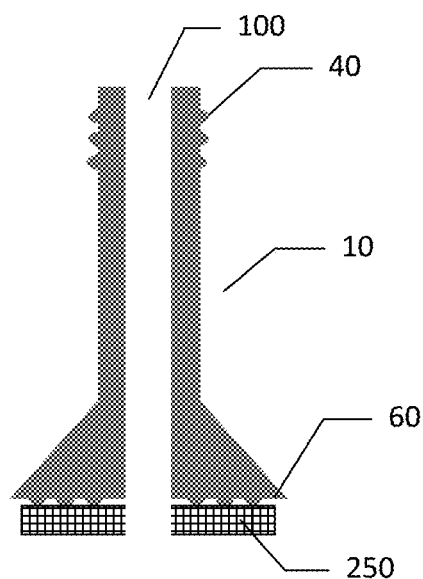

Referring now to FIGS. 6A-6D, fixation tool 10 is shown with annular structure such as a buttress 250, whereby: FIG. 6A shows annular structure or buttress 250, generally O-ring shaped in a perspective view; FIG. 6B shows schematic cross-sectional view of fixation tool 10 against buttress 250 with the diameter of flat face 60 being substantially equivalent to the diameter of buttress 250; FIG. 6C shows schematic cross-sectional view of fixation tool 10 against buttress 250 with the diameter of flat face 60 being smaller than the diameter of buttress 250, such as 10-25% smaller; FIG. 6D shows schematic cross-sectional view of fixation tool 10 against buttress 250 with the diameter of flat face 60 being larger than the diameter of buttress 250, such as 10-25% larger.

Figure 7A:
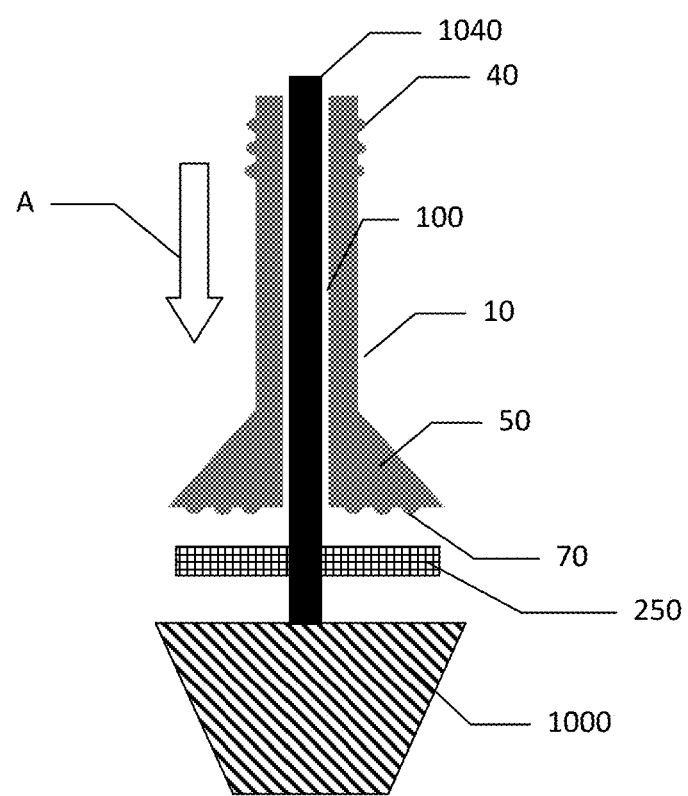
FIGS. 7A-7F show the sequence of performing anastomotic joining of tubular tissue lumens in a schematic cross-sectional side view.

Referring now to FIGS. 7A-7F, the sequence of steps using fixation tool 10 during anastomotic stapling of tissue is illustrated in schematic cross-sectional views. FIG. 7A shows buttress 250 installed over shaft 1040 in proximity to anvil 1000, with fixation tool 10 slidably positioned over shaft 1040 with flange 50 facing towards anvil 1000. Arrow A indicates direction of moving fixation tool 10.

Figure 7B:
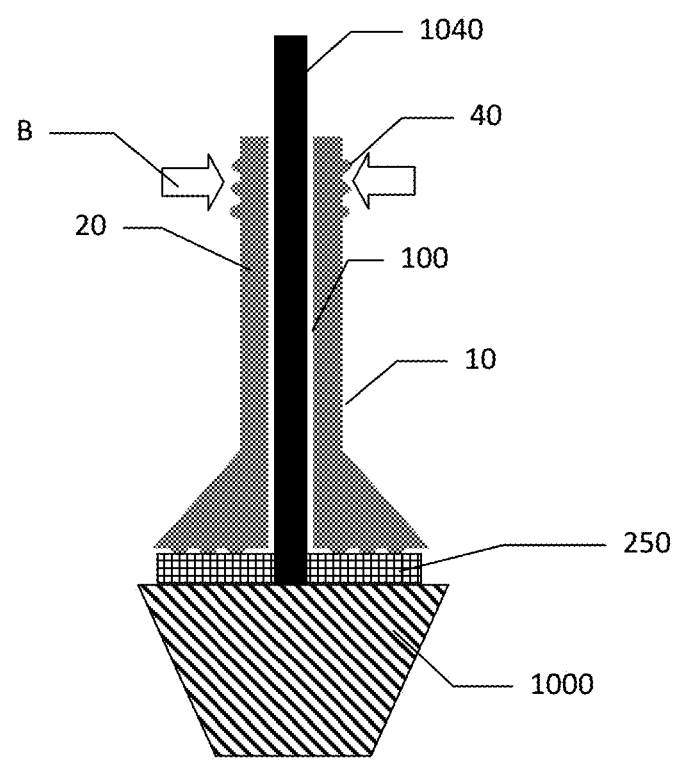

FIG. 7B shows buttress 250 fixated and immobilized against anvil 1000 by fixation tool 10 which holds buttress 250 against anvil 1000. Arrows B indicates direction of compressing or squeezing sleeve 20 to immobilize fixation tool 10 on shaft 1040.

Figure 7C:
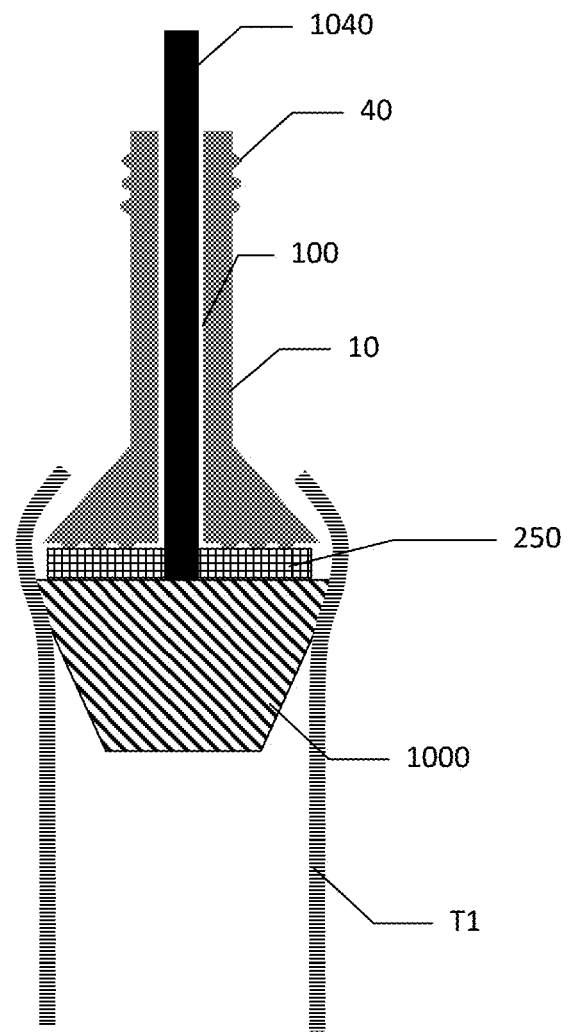

FIG. 7C shows insertion of anvil 1000 with buttress 250 fixated and immobilized against anvil 1000 by fixation tool 10 into tubular tissue T1, typically intestinal or colon tissue. T1 can have a purse string (not shown), which is used to partially approximate close tubular tissue around shaft 1040.

Figure 7D:
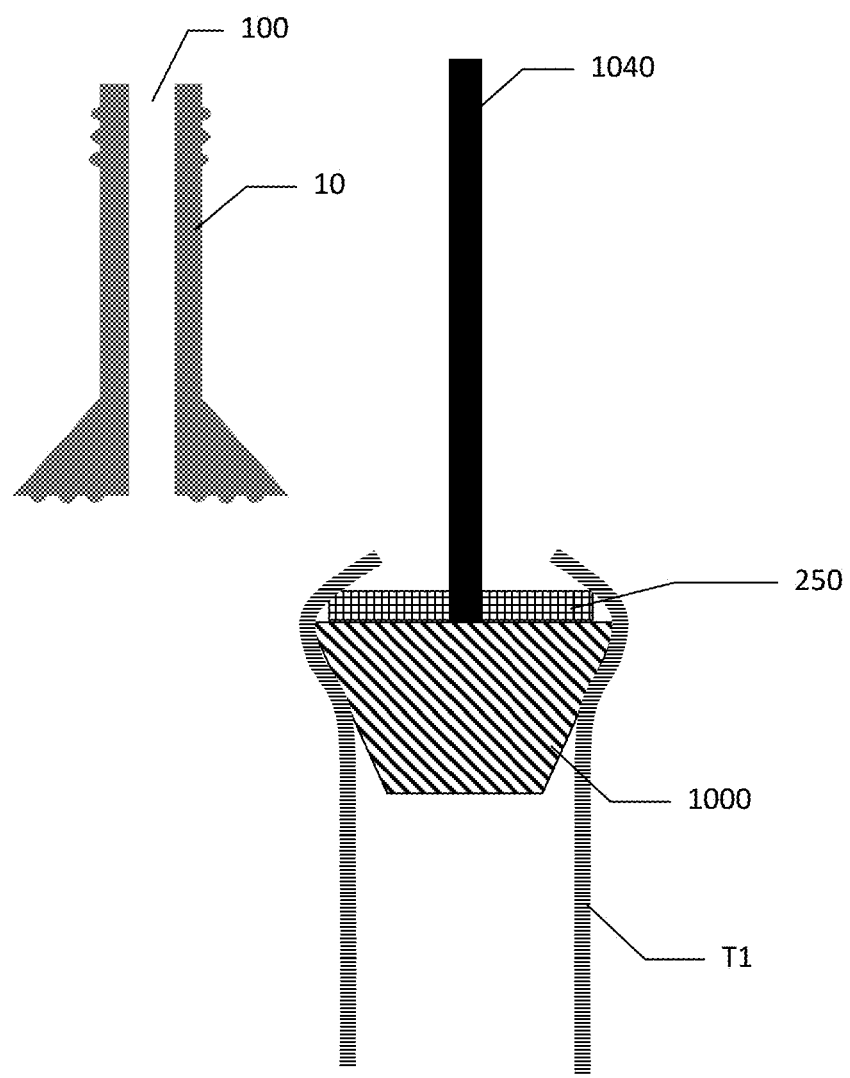

Fixation tool 10 is then carefully slidably removed from tubular tissue T1 along shaft 1040, leaving anvil 1000 and buttress 250 within tubular tissue T1, as shown in FIG. 7D.

Purse string (not shown) is then tightened resulting in closing of tubular tissue T1 around shaft 1040 and covering anvil 1000 and buttress 250. Shaft 1040 is then inserted into stapling head 600 which is disposed within tubular tissue T2.

Figure 7E:
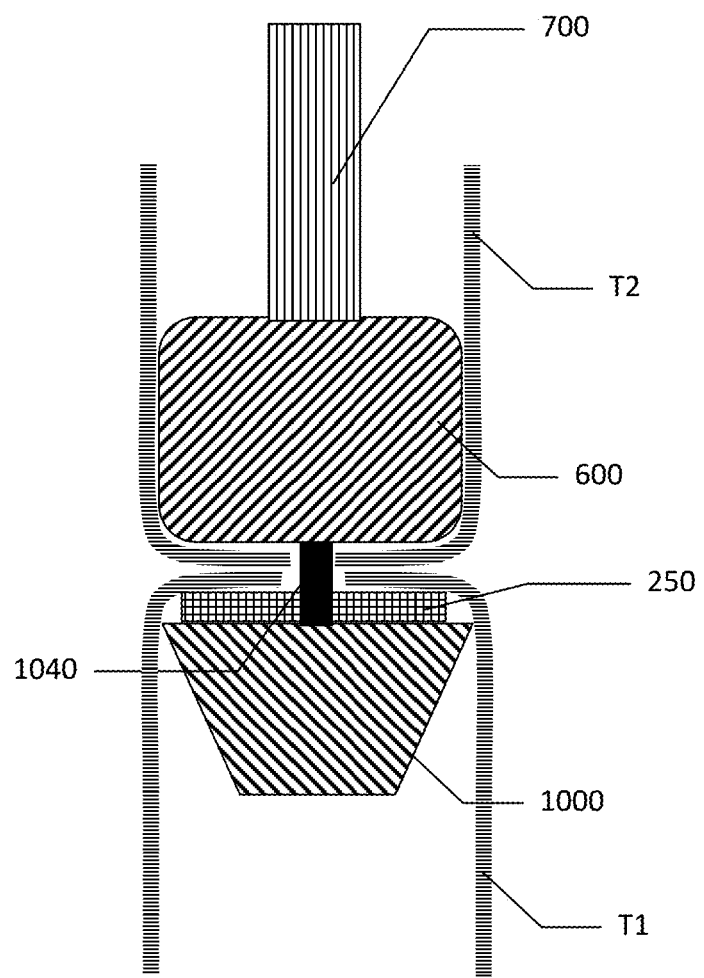
Figure 7F:
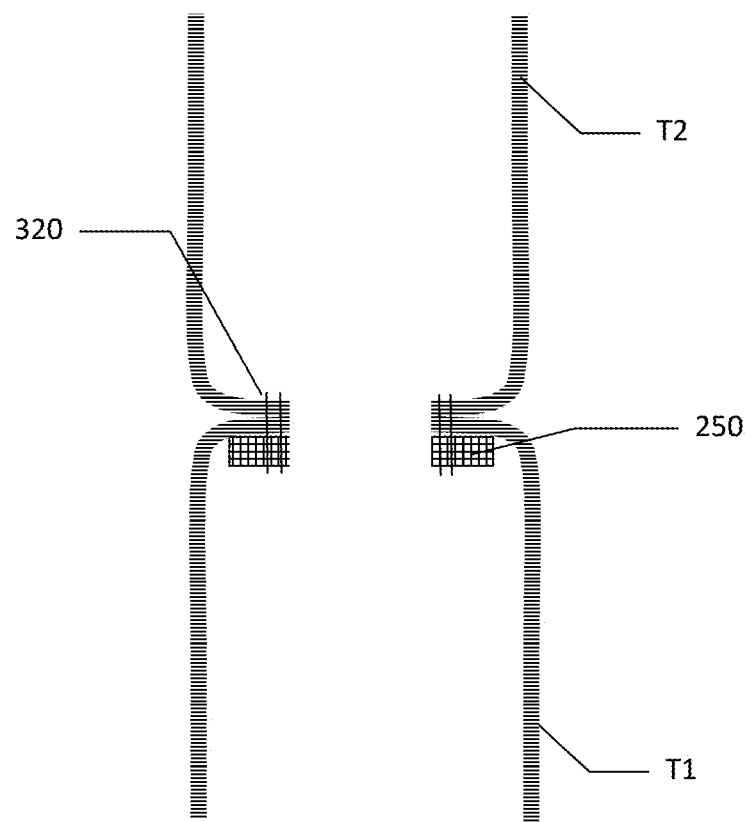

As shown in FIG. 7E, anvil 1000 with buttress 250 disposed within tubular tissue T1 and into stapling head 600 which is disposed within tubular tissue T2 are then approximated to each other, compressing tissue T1 and T2 between them, FIG. 7F shows staples 320 fired and anastomotic stapler removed, thus establishing anastomotic joint reinforced by buttress 250.

In operation, as shown above, a health practitioner performs the following steps:
  Positioning a buttress 250 and fixation tool 10 on anvil shaft 1040;
  Slidably advancing fixation tool 10 towards anvil 1000 on anvil shaft 1040;
  Immobilizing buttress 250 against anvil 1000 with fixation tool 10;
  Manually squeezing sleeve 20 to hold or temporarily lock fixation tool 10 on anvil shaft 1040;
  Inserting anvil 1000 with buttress 250 and fixation tool 10 into tubular tissue T1;
  Removing fixation tool 10 from tubular tissue T1 leaving anvil 1000 with buttress 250 inside tubular tissue T1;
  Approximating anvil 1000 with buttress 250 disposed within tubular tissue T1 and stapling head 600 which is disposed within tubular tissue T2;
  Compressing tissue T1 and T2 between stapling head 600 and anvil 1000 with buttress 250 disposed between stapling head 600 and anvil 1000 but within tissue T1;
  Firing anastomotic stapler, thus establishing anastomotic joint between tissues T1 and T2 reinforced by buttress 250.

Advantageously, as can be seen from FIG. 7F, buttress 250 is disposed within tissue T1 after the stapling.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

We claim:

1. A circular stapler comprising:
a) an anvil that is circular, the anvil having a flat facing surface;
b) a staple head assembly with an opposing flat surface;
c) an anvil shaft that joins the anvil and staple head assembly;
d) a buttress material positioned on said flat facing surface of said anvil, said buttress material immobilized against the anvil; and
e) a fixation tool having at a proximal end a sleeve that is elongated and cylindrical with an outer circumference and at a distal end a flange that is frustoconically shaped, wherein an interior axial opening traverses the entire length of the sleeve and the flange,
said flange terminating at the distal end with a flat face portion, said flat face portion having a diameter larger than diameter of the sleeve and a plurality of bumps disposed on said flat face portion,
said sleeve having at least two slits starting at the proximal end and extending along the sleeve towards the flange,
wherein said fixation tool comprises 20 to 80 of said bumps and three to eight grips that are parallel and circumferential.

2. The stapler of claim 1, wherein said grips are disposed at the proximal end of said sleeve, said grips comprising raised ridges or trenches along the outer circumference of the sleeve.

3. The stapler of claim 1 wherein said interior axial opening of the fixation tool fits over the anvil shaft of the circular stapler.

4. The stapler of claim 1 wherein the buttress material is bioabsorbable.

* * * * *